United States Patent [19]

Bastioli et al.

[11] Patent Number: 5,286,770
[45] Date of Patent: Feb. 15, 1994

[54] DISPOSABLE ABSORBENT ARTICLES

[75] Inventors: Catia Bastioli, Novara; Vittorio Bellotti, Fontaneto D'Agogna; Giancarlo Romano, Novara, all of Italy

[73] Assignee: Novamont S.P.A., Milan, Italy

[21] Appl. No.: 744,300

[22] Filed: Aug. 13, 1991

[30] Foreign Application Priority Data

Aug. 1, 1991 [EP] European Pat. Off. ......... 91112942.7

[51] Int. Cl.$^5$ ............... B32B 9/02; C08L 3/02; C08L 23/08; C08L 29/04
[52] U.S. Cl. ................ 524/52; 523/105; 523/125; 524/47; 524/51; 524/53; 524/215; 524/216; 604/370; 604/372
[58] Field of Search ............ 523/105, 125; 524/47, 524/51, 52, 53, 215, 216; 604/370, 372

[56] References Cited

U.S. PATENT DOCUMENTS

| | | | |
|---|---|---|---|
| 3,652,542 | 3/1972 | Hjermstad | 524/51 |
| 3,814,101 | 6/1974 | Kozak | 604/370 |
| 3,848,594 | 11/1974 | Buell | 128/284 |
| 3,850,652 | 11/1974 | Asaka et al. | 106/197.1 |
| 3,860,003 | 1/1975 | Buell | 128/287 |
| 4,589,876 | 5/1986 | Van Tilburg | 604/385 |
| 4,673,438 | 6/1987 | Wittwer et al. | 106/126 |
| 4,687,478 | 8/1987 | Van Tilburg | 604/387 |
| 4,863,655 | 9/1989 | Lacourse et al. | 264/53 |
| 4,900,361 | 2/1990 | Sachetto et al. | 106/213 |
| 4,906,495 | 3/1990 | Martini et al. | 428/286 |
| 4,973,504 | 11/1990 | Romberg et al. | 428/36.8 |
| 5,000,994 | 3/1991 | Romberg et al. | 428/36.8 |
| 5,035,930 | 6/1991 | Lacourse et al. | 428/35.6 |
| 5,043,196 | 8/1991 | Lacourse et al. | 428/35.6 |
| 5,095,054 | 3/1992 | Lay et al. | 524/52 |

FOREIGN PATENT DOCUMENTS

| | | | |
|---|---|---|---|
| 79802 | 10/1976 | Australia . | |
| 0032802 | 7/1981 | European Pat. Off. . | |
| 0282451 | 9/1988 | European Pat. Off. . | |
| 0298920 | 1/1989 | European Pat. Off. . | |
| 0327505 | 8/1989 | European Pat. Off. | 524/53 |
| 0304401 | 2/1989 | European Pat. Off. . | |
| 0326517 | 8/1989 | European Pat. Off. . | |
| 368103 | 9/1990 | European Pat. Off. . | |
| 0388924 | 9/1990 | European Pat. Off. | B32B 27/20 |
| 0391853 | 10/1990 | European Pat. Off. . | |
| 0400532 | 12/1990 | European Pat. Off. | C08L 23/08 |
| 0404723 | 12/1990 | European Pat. Off. . | |
| 0404727 | 12/1990 | European Pat. Off. . | |
| 0404728 | 12/1990 | European Pat. Off. . | |
| 0407350 | 1/1991 | European Pat. Off. . | |
| 0408501 | 1/1991 | European Pat. Off. . | |
| 0408502 | 1/1991 | European Pat. Off. . | |
| 0408503 | 1/1991 | European Pat. Off. . | |
| 0409781 | 1/1991 | European Pat. Off. . | |
| 0409782 | 1/1991 | European Pat. Off. . | |
| 0409783 | 1/1991 | European Pat. Off. . | |
| 0409788 | 1/1991 | European Pat. Off. . | |
| 0409789 | 1/1991 | European Pat. Off. . | |
| 9110671 | 9/1990 | PCT Int'l Appl. | 524/53 |
| WO91/02023 | 2/1991 | PCT Int'l Appl. . | |
| 9102024 | 2/1991 | PCT Int'l Appl. | 524/53 |
| 9102025 | 2/1991 | PCT Int'l Appl. | 524/53 |
| 2190093 | 5/1986 | United Kingdom . | |
| 8802313 | 2/1988 | United Kingdom . | |

OTHER PUBLICATIONS

European Search Report dated Mar. 31, 1992 in European Patent Application EP 91112942 with Communication dated Apr. 4, 1992 and one-page Annex.
International Search Report and one-page annex of PCT Pub. No. WO 90/10671.
*Chemical Abstracts*, vol. 7, No. 8, p. 47, Abstract No. 60151n, F. H. Otey et al., "Starch-based blown films" (Aug. 24, 1987).
Otey, F. H. et al., Ind. Eng. Chem. Res. 26(8):1659–1663 (1987), "Starch-Based Blown Films".

*Primary Examiner*—Paul R. Michl
*Assistant Examiner*—Andrew E. C. Merriam
*Attorney, Agent, or Firm*—Bryan Cave

[57] ABSTRACT

An absorbent article, such as diapers and the like, comprises a liquid pervious topsheet, a liquid impervious backsheet joined with said topsheet and an absorbent core positioned between said topsheet and said backsheet, said backsheet comprising a flexible starch based film comprising starch, a synthetic thermoplastic polymer of at least one ethylenically insaturated monomer, said polymer having repeating units provided with at least a polar group, wherein the starch and the polymer form an at least partially interpenetrated network, and moisture.

16 Claims, No Drawings

DISPOSABLE ABSORBENT ARTICLES

TECHNICAL FIELD

The present invention relates to disposable absorbent articles such as diapers, sanitary napkins, pantiliners, and the like, which are especially adapted for absorbing various bodily fluids. The articles herein comprise topsheet and/or backsheet materials that are designed to enhance their compostability.

BACKGROUND OF THE INVENTION

A wide variety of absorbent articles designed to be efficient for the absorption of body fluids such as blood, urine, menses, and the like, are known. Disposable products of this type generally comprise some sort of fluid-permeable topsheet material, an absorbent core, and a fluid-impermeable backsheet material.

Heretofore, such absorbent structures have been prepared using, for example, topsheet materials prepared from woven, nonwoven, or porous formed-film polyethylene or polypropylene materials. Backsheet materials typically comprise flexible polyethylene sheets. Absorbent core materials typically comprise wood pulp fibers or wood pulp fibers in combination with absorbent gelling materials.

One aspect of such absorbent articles that has recently been considered is their disposability. Although such products largely comprise materials which would be expected ultimately to degrade, and although products of this type contribute only a very small percentage of the total solid waste materials generated by consumers each year, nevertheless, there is currently a perceived need to devise such disposable products from materials which are compostable.

A conventional disposable absorbent product is already to a large extent compostable. A typical disposable diaper, for example, consists of about 80% of compostable materials, e.g., wood pulp fibers, and the like. In the composting process soiled disposable absorbent articles are shredded and commingled with organic waste prior to the composting per se. After composting is complete the non-compostable particles are screened out. In this manner even today's absorbent articles can successfully be processed in commercial composting plants. Nevertheless, there is a need for reducing the amount of non-compostable materials in disposable absorbent articles. There is a particular need to replace polyethylene backsheets in absorbent articles with liquid impervious films of compostable material, because the backsheet is typically the largest non-compostable component of a conventional disposable absorbent article.

It is, therefore, an object of the present invention to provide absorbent articles having a liquid impervious backsheet comprising a compostable polymer.

BACKGROUND ART

International Patent Applications WO 90/10671, WO 91/02025, WO 91/2024 and EP 400532 disclose biodegradable compositions based on starch and a synthetic thermoplastic polymer which can be formed into articles or a film.

Polymeric materials made from destructurized starch and a synthetic thermoplastic polymer which can be formed into articles and films are also disclosed by EP 327050, EP 0404723, EP 0404727, EP 408503.

In none of the above references it is suggested that the films are suitable for use in absorbent articles or that the biodegradability characteristics are such to make the materials suitable for composting.

SUMMARY OF THE INVENTION

The present invention provides an absorbent article comprising a liquid pervious topsheet, a liquid impervious backsheet joined with said topsheet and an absorbent core positioned between said topsheet and said backsheet, characterized in that said backsheet comprises a flexible starch based film comprising starch, a synthetic thermoplastic polymer of at least one ethylenically insaturated monomer, said polymer having repeating units provided with at least a polar group, wherein the starch and the polymer form an at least partially interpenetrated network, and moisture.

DETAILED DESCRIPTION OF THE INVENTION

The synthetic polymeric component includes polymers and copolymers having repeating units provided with at least a polar functional group such as hydroxy, alkoxy, carboxy, carboxyalkyl, alkyl carboxy and acetal.

Preferred polymeric components include polyvinyl alcohol and copolymers of an olephin selected from ethylene, propylene, isobutene and styrene with acrylic acid, vinyl alcohol and/or vinyl acetate.

The above olephin copolymers include ethylene copolymers having more than 50% by weight of ethylene and having melting points between 80° and 130° C. such as ethylene-acrylic acid, ethylene-vinyl alcohol, ethylene-vinyl acetate and mixtures thereof.

Particularly preferred are polyvinyl alcohol and ethylene-vinyl alcohol copolymers with ethylene contents of from 10 to 44% wt, preferably 28–40% wt, with various degrees of hydrolysis, produced by the hydrolysis of the corresponding polyvinyl acetate or ethylene-vinyl acetate respectively. The degree of hydrolysis of the ethylene-vinyl alcohol is preferably between 100 and 50%.

The alcoholic units of the polymers mentioned above may be partly or wholly modified to produce:

1) ethers resulting from reaction with:
ethylene oxide,
ethylene oxide substituted by alkyl radicals up to $C_{20}$ or by aromatic radicals,
acrylonitrile ($Ce^{2+}$ initiator),
acrylamide,
arylalkyl halides,
chloracetic acid,
methylchloromethyl ether,
silanes 2) inorganic and organic esters such as sulphates, nitrates, phosphates, arsenates, xanthates, carbamates, urethanes, borates, titanates, 3) organic esters resulting from reactions with aliphatic or aromatic acids, chloroacyls, particularly of fatty acids or anhydrides, 4) acetals and ketals produced by reaction with:
aliphatic aldehydes with up to 22 carbon atoms,
unsaturated aliphatic aldehydes with up to 22 carbon atoms,
chloroacetaldehyde,
glyoxal,
aromatic aldehydes,
cyclic aliphatic aldehydes, aliphatic ketones,
arylalkyl ketones,
alkylcycloalkyl ketones.

The reactions to produce the organic and inorganic esters and the acetals given above can easily be achieved as described in Chapter 9 and the literature cited in the publication "Polyvinyl alcohol" edited by C. a. Finch.

It is also possible to use polyvinyl alcohol and ethylene-vinyl alcohol multifunctional polymers (with ethylene contents of up to 44% by weight and degrees of hydrolysis of the acetate of between 100 and 50%) in which up to 50% of the ethylene may be substituted by co-monomers selected from the group consisting of:

propylene, isobutene, styrene, vinyl chloride, 1,1-dichloroethene, vinyl ethers of the formula $CH_2=CR-OR'$ in which R is hydrogen or a methyl group and R' is an alkyl group with from 1 to 18 carbon atoms, a cycloalkyl group or a polyether, acrylonitrile, methacrylonitrile, vinyl ketones of the formula $CH_2=CR-CO-CH_2-R'$ in which R is hydrogen or a methyl group and R' is hydrogen or a $C_1-C_6$ alkyl group, acrylic or methacrylic acid or their esters of the formula $CH_2=CR-COOR'$ in which R is hydrogen or a methyl group and R' is hydrogen or a $C_1-C_6$ alkyl group and the alkali metal or alkaline earth salts of these acids, vinyl derivatives of the formula $CH_2=CR-O-COR'$ in which R is hydrogen or a methyl group and R' is hydrogen, a methyl group, a methyl group mono-, bi- or tri-substituted with chloro or fluoro groups or $C_2-C_6$ alkyl groups, vinylcarbamates of the formula $CH_2=CR-CONR'R''$, in which R is hydrogen or a methyl group and R' and R'' are the same or different and are hydrogen or $C_1-C_3$ alkyl groups, maleic anhydride, fumaric anhydride, vinylpyrrolidone, vinylpyridine, or 1-vinylimidazole.

The copolymerisation is achieved with the use of radical initiators such as hydrogen peroxide, peroxysulphates and benzoyl peroxides, as described in the chapter "Polymerisation processes of vinyl esters" and the literature cited on pages 406 et. seq. of Volume 17 of the "Encyclopedia of Polymer Science and Engineering".

Compositions may also be used including starch, ethylene-vinyl alcohol copolymer, possibly modified, and hydrophobic polymers of polyethylene or of its vinyl copolymers such as those cited above, or aliphatic polyesters (e.g. polyvinyl acetate, polycaprolactone, polyhydroxybutyrate (PHP) and polyhydroxybutyrate valerate (PHBV), polylactic acid, polyethylene and polybutylene adipates or sebacates), polyethers (e.g. polyoxymethylene, polyoxyethylene, polyoxypropylene, polyphenylene oxide), polyamides (nylon 6, nylon 12 etc.), polyacrylonitrile, polyurethanes, polyester/polyurethane copolymers, polyester/polyamide copolymers, polyglycolide, hydrophilic polymers such as: polyvinyl pyrrolidone, polyoxazoline, cellulose acetates and nitrates, regenerated cellulose, alkyl cellulose, carboxymethyl cellulose, casein-type proteins and salts thereof, natural gums such as gum arabic, algin and alginates, chitin and chitosan.

The film composition may further comprise from about 1 to about 50% wt of a plasticizer or a mixture of platicizers, preferably from about 5% to about 25% wt.

Suitable plasticizers include:

a) polyols formed by from 1 to 20 repeating hydroxylated units each unit including from 2 to 6 carbon atoms, b) ethers, thioethers, inorganic and organic esters, acetals and amino-derivatives of polyols formed by from 1 to 20 repeating hydroxylated units each including from 2 to 6 carbon atoms, c) polyol reaction products having from 1 to 20 repeating hydroxylated units each including from 2 to 6 carbon atoms with chain extenders, d) polyol oxidation products having from 1 to 20 repeating hydroxylated units each including from 2 to 6 carbon atoms including at least one aldehydic or carboxilic functional group or mixtures thereof which are obtained by the reaction of the polyols in question with periodic acid, hypochlorite or lead tetra-acetate.

The aliphatic polyols of type a) include ethylene glycol, propylene glycol, glycerol, trimethylolpropane, pentaerithritol, erythritol, arabitol, adonitol, xylitol, mannitol, iditol, galactitol, allitol, sorbitol, polyvinyl alcohol with from 3 to 20 repeating units and polyglycerol formed by from 2 to 20, preferably from 2 to 5, monomer units including mixtures of various oligomers.

Among the polyols of type b), mono- and di-esters and mono- and di-ethers of the compounds mentioned in the above paragraph are preferred and particularly preferred are their, mono- and di-ethoxylate, mono- and di-propoxylate and mono- and di-acetate derivatives, most preferably sorbitol acetate, sorbitol diacetate, sorbitol monoethoxylate, sorbitol dipropoxylate.

The term "polyol" is intended to include mono- and polysaccharides with up to 20 monosaccharide units.

The following monosaccharides come into consideration pentoses and their derivatives such as arabinose, lycose, ribose and xylose and, preferably, monoethers and monoester thereof, aldohexoses and ketohexoes such as glucose, fructose, mannose, allose, altrose, galactose, gulose, their etherified or esterified derivatives, particularly monoethoxylate and monopropoxylate derivatives and monoesters, particularly of acetic acid.

The polysaccharides include compounds having up to 20 repetitive units with molecular weights up to that of dextrin.

Compounds which have vapour pressures lower than that of glycerine at ambient temperature (25° C.) and which are soluble in water are generally preferred as the effective plasticizer.

The starch used in the polymeric compositions is preferably a native starch, particularly maize and potato starch, but the term starch is intended also to include physically and chemically modified starches such as those cited in EP-A-413798 and EP-A-400532. The term "native" starch includes waxy starch and amylostarch.

The native starch has an intrinsic water content of about 9-15% wt.

Additional water may be added to the starch-polymer composition during processing in a total amount of up to 40% wt referred to the starch-water system.

The intrinsic water content of starch is however per se sufficient in the presence of a high boiling plasticizer, (boiling point higher than 150° C.), to provide, under the processing conditions, for the formation of a homogeneous termoplastic melt of interpenetrated starch and synthetic polymer suitable for extrusion into a film as described in EP 400532.

The polymeric material may also include agents which can destroy hydrogen bonds, such as urea which may be added to the starch and copolymer mixture in quantities of between 0.5 and 20% of the weight of the entire composition, preferably 2-7% wt.

The polymeric material may also include cross-linking agents, such as aldehydes, ketones and glyoxals, process coadjuvants and release and lubricating agents normally incorporated in compositions for moulding or extrusion, such as fatty acids, fatty-acid esters, higher alcohols, polythene waxes, antioxidants, opacifiers and stabilisers.

The amount of water in the starch based film (as extruded) used as backsheet in the absorbent articles of the present invention usually does not exceed 10% wt. and is preferably from 0.5 to 6% wt, most preferably from 2 to 4% wt.

Preferred compositions for use in the backsheet of the claimed absorbent articles comprise from about 20 to about 70% wt starch (dry basis); from about 10 to about 50% wt of synthetic polymer or copolymer; from about 2 to about 40% wt high boiling plasticizer or mixture of plasticizers; from about 0 to about 10% urea and from about 1 to about 5 water (after extrusion, before conditioning).

Highly preferred compositions comprise:
a) from 30 to 60% wt starch (dry basis);
b) from 20 to 50% wt of a polymer selected from ethylene-vinyl alcohol (with ethylene content of from 10 to 44% wt, most preferably 28–40% wt), polyvinyl alcohol and ethylene-acrylic acid and mixtures thereof;
c) from 5 to 25% wt of a high boiling plasticizer or mixtures of plasticizers;
d) from 2 to 7% wt urea and from 2 to 4% wt moisture (as extruded, before conditioning).

If component b) consists of a mixture of ethylene-vinyl alcohol and ethylene-acrylic acid, the latter is preferably used in the amount of 5 to 15% wt referred to ethylene-vinyl alcohol.

The polymeric composition is preferably prepared by the mixing of the components cited above in an extruder heated to a temperature generally between 100° and 220° C. The composition supplied to the extruder includes water due to the intrinsic water content of the starch used (9–15% by weight) and water may be added as appropriate. If the overall amount of water in the composition fed to the extruder exceeds the values which have been above defined for the backsheet, the water content of the total composition is preferably reduced by intermediate degassing during the extrusion.

The pressures to which the blend is subjected during the heat treatment are those typical for extrusion in single-and twin-screw extruders. Although the process is preferably carried out in an extruder, the starch, synthetic polymer and plasticiser may be mixed by any device which ensure conditions of temperature and shear stress suitable to render the starch and the polymer used compatible from a rheological point of view.

If synthetic polymers with high melting point, such as, for example, polyvinyl alcohol and ethylene-vinyl alcohol copolymer with ethylene contents no greater that 40% by weight are used, in particular, the plasticizers described also perform an important function in the process which leads to the formation of a composition with an (at least partially) interpenetrated structure. The melting point of these polymers (160°–200° C.) are so high that complete interpenetration with the starch molecules is impossible; the addition of plasticizers common to the starchy and polymeric components lowers the melting points of the synthetic polymers and at the same time changes their rheological behaviour.

The preferred method of preparing the compositions for the backsheet of the absorbent articles of the invention includes the following steps:
swelling the starch and synthetic polymer by means of the plasticizers and possibly water at a temperature between 80° and 180° C. with a dynamic change in their melting point and rheological behaviour; this effect can be achieved, for example, during a first stage of the transportation of the components in an extruder, for periods of the order of 2 to 50 seconds,
subjecting the mixture to shearing conditions corresponding to similar viscosity values of the two components so as to cause the interpenetration of the molecules of the two components,
degassing the mixture freely, under controlled pressure or under vacuum to produce a melt at a temperature of 140°–180° C. with a liquid content such that bubbles are not created at atmospheric pressure, that is, for example, at the output of the extruder.

The melt may be directly extruded as a film with the use of an extruder fitted with a film blowing head or it may be extruded and formed into pellets for subsequent processing into a film by conventional techniques.

The whole method requires a pressure of between 0.5 and 10 MPa, preferably between 1 and 5 MPa.

As stated, the thermoplastic composition is preferably prepared by directly mixing the above cited components; the starch may, however, also be treated beforehand in the presence of a plasticizer, possibly with added water, at a temperature of from 100° to 220° C. to produce a thermoplastic starch. This starch can be mixed with the synthetic polymer and a further quantity of plasticizers in a second step. For polyvinyl alcohol and ethylene-vinyl alcohol copolymer, a portion of the total quantity of plasticizers is added at the start of the mixing of the pretreated starch and the synthetic polymer since the plasticizer itself has to be available to modify the melting point and rheological behaviour of the polymer in order to make it compatible with the starch.

Preferably the flexible film constituting the backsheet is a laminated film comprising a first layer of a polymeric starch based material, such as above defined, and a second layer of a hydrophobic material adhering to the first.

In a preferred embodiment of the invention, the hydrophobic material constituting the second layer consists essentially of a polymeric coating of polyparaxylylene and/or substitution derivatives thereof, deposited on the film constituting the first layer by chemical vapour deposition. The thickness of the second layer may vary within wide limits and, according to the desired barrier properties to be obtained, thicknesses from about 0.01 $\mu$m to about 40 $\mu$m are preferred, preferably from 0.1 to 10 $\mu$m.

The technology of the application of polymeric polyparaxylylene coatings is known and is described, for example, in patent application No. EP-A-O 302 457, but with reference to substrates of a definitely hydrophobic nature.

The paraxylylene radical used corresponds to the formula:

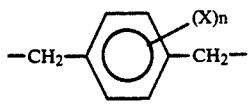 (I)

in which:
X is a $C_1$–$C_6$ alkyl group, a $C_6$–$C_{10}$ aryl group, a $C_7$–$C_{16}$ arylalkyl group, a haloalkyl or haloarylalkyl group, an acetoxy group, an aminoalkyl group, an arylamino group, a cyano group, an alkoxy group, a hydroxy group, a nitro group, a halogen group, a sulphonic radical, a sulphonic ester radical, a phosphorus-based substituent, a sulphide group, an alkylsulphoxide group or a hydrogen atom, and
n is 0 or a whole number from 1 to 4.

Since their reactivity causes great difficulties in their storage and handling, for practical applications, the preferred starting compounds are the dimers of paraxylylene or (2,2)-paracyclophane and of their derivatives conforming to the possible substitutions indicated above.

The dimers of paraxylylene are in fact stable crystalline solids at ambient temperature and can easily be stored and handled. The dimers can be prepared by conventional methods, for example, by the pyrolysis of paraxylylene or from the corresponding paramethylbenzyl trimethylammonium hydroxide by Hofmann degradation.

During the application of the polymeric coating by vapour deposition under vacuum, the paraxylylene dimers are subjected to pyrolytic cracking under vacuum at temperatures higher than 400° C. to give reactive radicals of formula (I) which are made to condense on the surface of the substrate producing homopolymers or copolymers of paraxylylene according to the dimer use.

Small quantities of the other monomers such a maleic anhydride or chloroprene which polymerise on the surface of the film of material with a starchy matrix may be used with (2,2)-paracyclophan and its derivatives. The bivalent paraxylylene radicals condense and polymerise almost instantaneously on the surface of the first layer forming a compact polymer.

The structural principles of devices for the deposition of vapours of bivalent reactive paraxylylene radicals are known and are described, for example, in Kirk-Othmer Encyclopedia of Chemical Technology, Third Ed., Volume 24, pages 746–747. Such a device includes an evaporation-cracking furnace in which the (2,2)paracyclophane or a derivative thereof is inserted, and which is in communication with a deposition chamber which is kept a temperature lower than the condensation temperature of the specific paraxylylene derivative.

The deposition chamber may conveniently be modified for the purposes of the present application to enable the continuous or semi-continuous deposition of the polymeric coating.

The application of a paraxylylene monomer is compatible with the optional use of agents such as, for example, siloxane compounds or derivatives of phosphorus usually used in the deposition under vacuum technique for promoting adhesion.

By way of example, preferred paraxylylene monomers are chloroparaxylilene, dichloroparaxylylene, cyanoparaxylylene, iodoparaxylylene, fluoroparaxylylene, hydroxymethylparaxylylene, ethylparaxylylene, methylparaxylylene, carbomethoxyparaxylylene, and mixtures thereof.

In an alternative embodiment of the invention, the hydrophobic material used for the second layer is a polymer containing free acid groups, preferably an ethylene-acrylic acid, or an ethylene-acrylic acid-alkyl acrylate copolymer.

For its application to the first layer with a starchy matrix, the polymer is salified by a base, preferably ammonium hydroxide, and is thus made soluble in water. Surfactants, emulsified waxes, silica, polyoxyethylenes, polyacrylic acids, polyvinylpyrrolidone, polyvinyl alcohol, etc. may be added to the solution to increase its ability to wet the starchy film and to reduce the stickiness of the coating. The solution thus obtained is spread on the first layer by a technique similar to varnishing or spray-coating and undergoes heat treatment at a temperature and for a period of time sufficient to remove the aqueous solvent and eliminate the salifying groups thus producing a polymeric coating which is insoluble in water.

In a further alternative embodiment of the invention, the hydrophobic material used for the second layer is constituted by a polyhydroxyalkanoate polymer, particularly PHB (polyhydroxybutyrate), PHB/V (polyhydroxybutyrate/valerate), lactic acid homopolymers and lactic acids copolymerised with glycolic acids or with $\Sigma$-caprolactone, polyethylene-vinyl alcohol, or polyethylene-vinyl acetate.

The coating can be achieved by coextrusion, by blowing or casting technology.

These embodiments also produced hydrophobic coatings with good barrier properties and good adhesion to the starchy substrate.

The films for use as backsheets in the absorbent articles typically have a thickness of from 0.01 mm to about 0.02 mm, preferably 0.012 mm to about 0.051 mm.

This films material is used as a liquid impervious backsheet in absorbent articles, for example, disposable diapers. Typically, the liquid impervious backsheet is combined with a liquid pervious topsheet and an absorbent core is positioned between the topsheet and the backsheet, optionally with elastic members and tape tab fasteners. While the topsheet, the backsheet, the absorbent core and elastic members may be assembled in a variety of well known configurations, a preferred diaper configuration is described generally in U.S. Pat. No. 3,860,003, entitled "Contractible Side Portion for Disposable Diaper" which issued to Kenneth B. Buell on Jan. 14, 1975 and which patent is incorporated herein by reference.

The topsheet is compliant, soft-feeling, and non-irritating to the wearer's skin. Further, the topsheet is liquid pervious, permitting liquids to readily penetrate through its thickness. A suitable topsheet may be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably the topsheet is made of a hydrophobic material to isolate the wearer's skin from liquids in the absorbent core.

A particularly preferred topsheet comprises staple-length polypropylene fibers having a denier of about 1.5 such as Hercules type 151 polypropylene marketed by Hercules, Inc. of Wilmington, Del. As used herein, the term "staple-length fibers" refers to those fibers having a length of at least about 15 mm.

There are a number of manufacturing techniques which may be used to manufacture the topsheet. For example, the topsheet may be woven, nonwoven, spunbonded, carded, or the like. A preferred topsheet is carded, and thermally bonded by means well known to those skilled in the fabrics art. Preferably, the topsheet has a weight from about 18 to about 25 g/m$^2$, a minimum dried tensile strength of at least about 400 g/cm in the machine direction, and a wet tensile strength of at least about 55 g/cm in the cross-machine direction.

The topsheet and the backsheet are joined together in any suitable manner. As used herein the term "joined" encompasses configurations whereby the topsheet is directly joined to the backsheet by affixing the topsheet directly to the backsheet, and configurations whereby the topsheet is indirectly joined to the backsheet by affixing the topsheet to intermediate members which in turn are affixed to the backsheet. In a preferred embodiment, the topsheet and the backsheet are affixed directly to each other in the diaper periphery by attachment means such as an adhesive or any other attachment means as known in the art. For example, a uniform, continuous layer of adhesive, a patterned layer of adhesive, or an array of separate lines or spots of adhesive may be used to affix the topsheet to the backsheet.

Tape tab fasteners are typically applied to the back waistband region of the diaper to provide a fastening means for holding the diaper on the wearer. The tape tab fasteners can be any of those well known in the art, such as the fastening tape disclosed in U.S. Pat. No. 3,848,594, issued to Kenneth B. Buell on Nov. 19, 1974, the disclosures of which are incorporated herein by reference. These tape tab fasteners or the diaper fastening means are typically applied near the corners of the diaper.

Preferred diapers have elastic members disposed adjacent the periphery of the diaper, preferably along each longitudinal edge so that the elastic members tend to draw and hold the diaper against the legs of the wearer. The elastic members are secured to the diaper in an elastically contractible condition so that in a normally unrestrained configuration the elastic members effectively contract or gather the diaper. The elastic members can be secured in an elastically contractible condition in at least 2 ways. For example, the elastic members may be stretched and secured while the diaper is in an uncontracted condition. Alternatively, the diaper may be contracted, for example, by pleating, and the elastic members secured and connected to the diaper while the elastic members are in their relaxed or unstretched condition.

The elastic members may take a multitude of configurations. For example the width of the elastic members may be varied from about 0.25 mm to about 25 mm or more; the elastic members may comprise a single strand of elastic material or the elastic member may be rectangular or curvilinear. Still further, the elastic members may be affixed to the diaper in any of several ways which are known in the art. For example the elastic members may be ultrasonically bonded, heat and pressure sealed into the diaper using a variety of bonding patterns, or the elastic members may simply be glued to the diaper.

The absorbent core of the diapers is positioned between the topsheet and backsheet. The absorbent core may be manufactured in a wide variety of sizes and shapes (e.g., rectangular, hour-glass, asymmetrical, etc.) and from a wide variety of materials. The total absorbent capacity of the absorbent core should, however, be compatible with the designed liquid loading for the intended use of the absorbent articles or diaper. Further, the size and absorbent capacity of the absorbent core may vary to accommodate wearers ranging from infants through adults.

A preferred embodiment of the diaper has a modified hour-glass shaped absorbent core. The absorbent core is preferably an absorbent member comprising a web or batt of airfelt, wood pulp fibers, and a particulate absorbent polymeric composition disposed therein.

Other examples of absorbent articles according to the present invention are sanitary napkins designed to receive and contain vaginal discharges such as menses. Disposable sanitary napkins are designed to be held adjacent to the human body through the agency of a garment, such as an undergarment or a panty or by a specially designed belt. Examples of the kinds of sanitary napkins to which the present invention is readily adapted are shown in U.S. Pat. No. 4,687,478, entitled "Shaped Sanitary Napkin With Flaps" which issued to Kees. J. Van Tilburg on Aug. 18, 1987 and U.S. Pat. No. 4,589,876, entitled "Sanitary Napkin" which issued to Kees J. Van Tilburg on May 20, 1986, the disclosures of both patents being incorporated herein by reference. It will be apparent that the starch based polymeric films described herein may be used as the liquid impervious backsheet of such sanitary napkins. On the other hand it will be understood the present invention is not limited to any specific sanitary napkin configuration or structure.

In general, sanitary napkins comprise a liquid impervious backsheet, a liquid pervious topsheet, and an absorbent core placed between the backsheet and the topsheet. The backsheet is one of the starch based films described herein above. The topsheet may comprise any of the topsheet materials discussed with respect to diapers.

The absorbent articles according the present invention are compostable to a greater extent than conventional absorbent articles which employ a polyolefin, typically a polyethylene backsheet.

We claim:

1. An absorbent article comprising:
   (a) a liquid pervious topsheet;
   (b) a liquid impervious backsheet joined to the topsheet, wherein the backsheet comprises a flexible starch-based film comprising:
   (i) starch;
   (ii) at least one synthetic thermoplastic polymer selected from the group consisting of
   (aa) polyvinyl alcohol; (bb) copolymers of an olefin selected from the group consisting of ethylene, propylene, isobutene, styrene and combinations thereof with acrylic acid, vinyl alcohol, vinyl acetate, and combinations thereof; and (cc) combinations thereof;
   (iii) from 0.5 to 20 weight percent urea based on the total weight of the film;
   (iv) moisture; and
   (v) 5-25 percent plasticizer by weight based on the total weight of the film, wherein the plasticizer is selected from the group consisting of mono-ethoxylate, di-ethoxylate, mono-propoxylate, di-propoxylate, mono-acetate derivatives of sorbitol, di-acetate derivatives of sorbitol, and combinations thereof;

wherein the (i) starch and the (ii) at least one polymer form an at least partially interpenetrated network; and
(c) an absorbent core positioned between the topsheet and the backsheet.

2. An absorbent article comprising:
(a) a liquid pervious topsheet;
(b) a liquid impervious backsheet joined to the topsheet, wherein the backsheet comprises a laminated film comprising a first layer of a starch-based film and a second layer consisting essentially of a polymeric coating of polyparaxylylene and/or substitution derivatives thereof, wherein the first layer and the second layer adhere to each other; and
(c) an absorbent core positioned between the topsheet and the backsheet.

3. An absorbent article comprising:
(a) a liquid pervious topsheet;
(b) a liquid impervious backsheet joined to the topsheet, wherein the backsheet comprises a flexible starch-based film comprising:
   (i) starch;
   (ii) at least one synthetic thermoplastic polymer derived from at least one ethylenically unsaturated monomer, wherein the polymer has repeating units having at least one polar group;
   (iii) a high boiling point plasticizer selected from the group consisting of monoethoxylate; di-ethoxylate; mono-propoxylate; di-propoxylate; mono- and di-acetate derivatives of a polyol selected from the group consisting of sorbitol, xylitol, mannitol, iditol, galactitol, adonitol, arabitol, erythritol, pentaerythritol, and combinations thereof; and combinations thereof; and
   (iv) moisture;
   wherein the (i) starch and the (ii) at least one polymer form an at least partially interpenetrated network; and
(c) an absorbent core positioned between the topsheet and the backsheet.

4. An absorbent article comprising:
(a) a liquid pervious topsheet;
(b) a liquid impervious backsheet joined to the topsheet, wherein the backsheet comprises a flexible starch-based film comprising:
   (i) starch;
   (ii) polyethylene-vinyl alcohol and an aliphatic polyester;
   (iii) from 0.5 to 20 weight percent urea based on the total weight of the film; and
   (iv) moisture;
   wherein the (i) starch and the (ii) at least one polymer form an at least partially interpenetrated network; and
(c) an absorbent core positioned between the topsheet and the backsheet.

5. An absorbent article comprising:
(a) a liquid pervious topsheet;
(b) a liquid impervious backsheet joined to the topsheet, wherein the backsheet comprises a flexible starch-based film comprising:
   (i) starch;
   (ii) polyethylene-vinyl alcohol and an aliphatic polyester;
   (iii) from 0.5 to 20 weight percent urea based on the total weight of the film;
   (iv) moisture; and
   (v) 1-50 percent by weight plasticizer based on the total weight of the film, wherein the plasticizer is selected from the group consisting of (aa) polyols having 1-20 repeating hydroxylated units wherein each unit has 2-6 carbon atoms; (bb) ethers, thioethers, inorganic esters, organic esters, acetals and/or amino-derivatives of polyols having 1-20 repeating hydroxylated units wherein each unit has 2-6 carbon atoms; (cc) polyol reaction products having 1-20 repeating hydroxylated units wherein each unit has from 2-6 carbon atoms with chain extenders; (dd) polyol oxidation products comprising 1-20 repeating hydroxylated units wherein each unit has 2-6 carbon atoms, and wherein the polyol oxidation products comprise at least one aldehydic and/or carboxylic functional group that is obtained by reacting polyols with periodic acid, hypochlorite and/or lead tetraacetate; and (ee) combinations thereof;
   wherein the (i) starch and the (ii) at least one polymer form an at least partially interpenetrated network; and
(c) an absorbent core positioned between the topsheet and the backsheet.

6. An absorbent article comprising:
(a) a liquid pervious topsheet;
(b) a liquid impervious backsheet joined to the topsheet, wherein the backsheet comprises a flexible starchbased film comprising:
   (i) starch;
   (ii) at least one synthetic thermoplastic polymer derived from at least one ethylenically unsaturated monomer, wherein the polymer has repeating units having at least one polar group;
   (iii) from 0.5 to 20 weight percent urea based on the total weight of the film;
   (iv) moisture; and
   (v) 1-50 percent by weight plasticizer based on the total weight of the film wherein the plasticizer is selected from the group consisting of monoethoxylate; di-ethoxylate; mono-propoxylate; di-propoxylate; mono-acetate derivatives of a polyol; di-acetate derivatives of a polyol; and combinations thereof; wherein the polyol is selected from the group consisting of sorbitol; xylitol; mannitol; iditol; galactitol; adonitol; arabitol; erythritol; pentaerythritol; trimethylolpropane; and combinations thereof;
   wherein the (i) starch and the (ii) at least one polymer form an at least partially interpenetrated network; and
(c) an absorbent core positioned between the topsheet and the backsheet.

7. An absorbent article as defined in claim 1 wherein the (iv) moisture is present in amounts of less than 6 percent by weight of the total weight of the film.

8. An absorbent article as defined in claim 7 wherein the (iv) moisture is present in amounts of 2-4 percent by weight of the total weight of the film.

9. An absorbent article as defined in claim 1 wherein the hydrophobic material of the second layer comprises a polymer containing free acid groups.

10. An absorbent article as defined in claim 9 wherein the polymer comprises an ethylene-acrylic acid or an ethylene-acrylic acid-alkylacrylate copolymer.

11. An absorbent article as defined in claim 1 wherein the hydrophobic material of the second layer comprises a polymer selected from the group consisting of a polyhydroxyalkanoate polymer, a lactic acid homopolymer, a copolymer of lactic acids copolymerized with glycolic acids or with epsilon caprolactone, polyethylene-vinyl alcohol, polyethylene-vinyl acetate, and combinations thereof.

12. An absorbent article as defined in claim 1 wherein the starch-based film comprises:
   (i) from 20 to 70 weight percent starch on a dry basis;
   (ii) from 10 to 50 weight percent synthetic thermoplastic polymer;
   (iii) from 2 to 10 weight percent urea;
   (iv) from 0.5 to 6 weight percent moisture after extrusion but before conditioning; and
   (v) from 2 to 40 weight percent plasticizer.

13. An absorbent article as defined in claims 4 or 5 wherein the aliphatic polyester is selected from the group consisting of polyvinylacetate, polycaprolactone, polyhydroxybutyrate, polyhydroxybutyrate valerate, polylactic acid, polybutylene adipate, polybutylene sebacate, polyethylene adipate, polyethylene sebacate and combinations thereof.

14. An absorbent article as defined in claims 4 or 5 wherein the starch-based film comprises:
   (ii) a mixture of polyethylene-vinyl alcohol and polycaprolactone; wherein the polyethylene-vinyl alcohol comprises not more than 44 weight percent ethylene.

15. An absorbent article as defined in claims 2 or 1 wherein the starch-based film comprises:
   (i) from 30 to 60 weight percent starch on a dry basis;
   (ii) from 20 to 50 weight percent of a polymer selected from the group consisting of (aa) ethylene-vinyl alcohol having an ethylene content of from 10 to 44 weight percent; (bb) polyvinyl alcohol; (cc) ethylene-acrylic acid; and (dd) combinations thereof;
   (iii) from 2 to 10 weight percent urea;
   (iv) from 2 to 4 weight percent moisture after extrusion but before conditioning; and
   (v) from 5 to 25 weight percent high boiling point plasticizer.

16. The article of claim 1 or claim 4 wherein the backsheet comprises a laminated film comprising said flexible starch-based film and a second layer comprising a hydrophobic material, wherein the first layer and the second layer adhere to each other.

* * * * *